United States Patent
Calderwood (12)

(10) Patent No.: US 6,402,511 B1
(45) Date of Patent: Jun. 11, 2002

(54) PATHOGEN BARRIER WITH OPTICALLY TRANSPARENT END

(76) Inventor: Mitchell C. Calderwood, 340 S. Kellogg, Suite G, Goleta, CA (US) 93117

( * ) Notice: Subject to any disclaimer, the term of this patent is extended or adjusted under 35 U.S.C. 154(b) by 0 days.

(21) Appl. No.: 09/243,375

(22) Filed: Feb. 1, 1999

Related U.S. Application Data

(63) Continuation-in-part of application No. 08/503,038, filed on Jul. 17, 1995, now Pat. No. 5,865,621.

(51) Int. Cl.[7] .................................................. A61C 3/00
(52) U.S. Cl. ......................................... 433/29; 433/116
(58) Field of Search .................................... 433/29, 116

(56) References Cited

U.S. PATENT DOCUMENTS

| | | | | |
|---|---|---|---|---|
| 3,794,091 A | * | 2/1974 | Ersek et al. | 150/52 R |
| 4,385,344 A | * | 5/1983 | Gonser | 362/32 |
| 5,228,851 A | * | 7/1993 | Burton | 433/116 |
| 5,328,368 A | * | 7/1994 | Lansing et al. | 433/29 |
| 5,484,283 A | * | 1/1996 | Franetzki | 433/29 |

FOREIGN PATENT DOCUMENTS

| | | | | |
|---|---|---|---|---|
| EP | | 539315 | * 4/1993 | 433/29 |

* cited by examiner

*Primary Examiner*—John J. Wilson
(74) *Attorney, Agent, or Firm*—Sanford J. Piltch

(57) ABSTRACT

A disposable pathogen barrier of a material which is highly elastic and stretchable, yet tear-resistant, and capable of being placed in proximate contact and covering an entirety of a variety of elongated, tubular-shaped intra-oral medical or dental tools or implements which emit lightwaves in pre-determined ranges without distorting, interrupting or shifting the wavelength of the emitted light, or the receiving of reflected light, by the use of, in a first embodiment, an optically transmissive end and, in a second embodiment, an optically clear film to provide the required range of transmissivity of light.

4 Claims, 2 Drawing Sheets

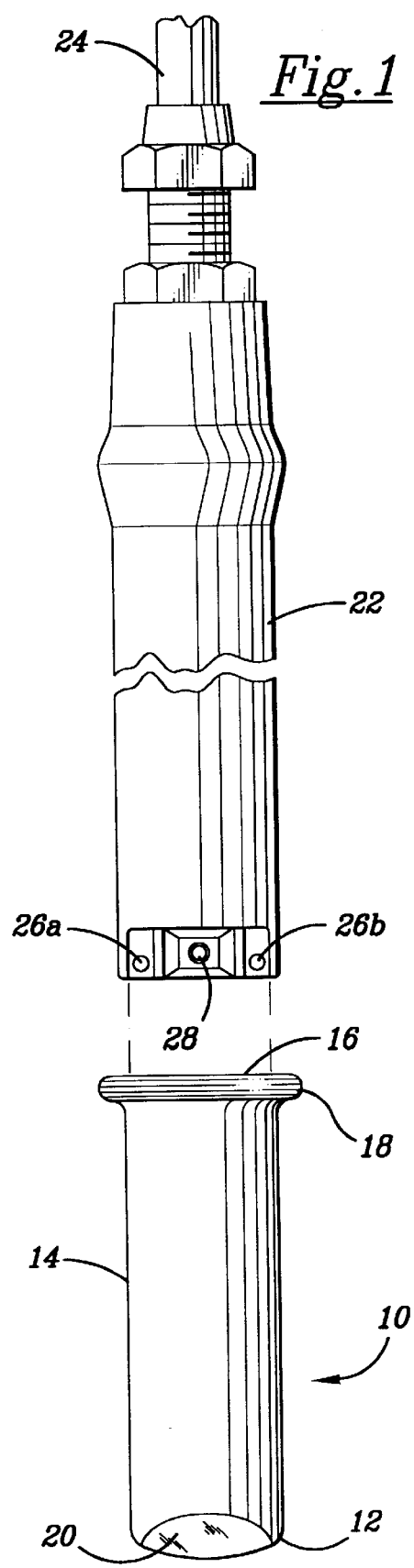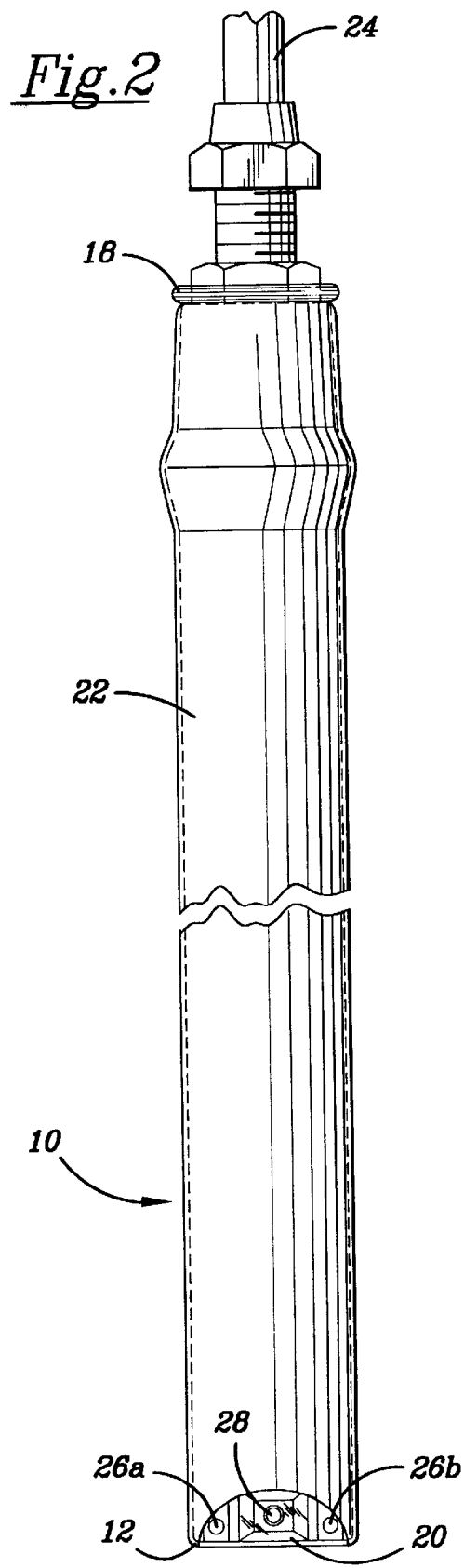

PATHOGEN BARRIER WITH OPTICALLY TRANSPARENT END

This application is a CIP of Ser. No. 08/503,038 Jul. 17, 1995 U.S. Pat. No. 5,865,621.

BACKGROUND OF THE INVENTION

Dental practitioners have been aware for years that the repeated handling of a dental tool by gloved or ungloved hands after either the dental practitioner's or the hygienist's hands have been in or around the mouths of several different patients without proper sterilization can bring about the spread of contagious diseases. Such contagious or communicable diseases are borne in or on the body fluids and/or tissues which may become attached to the tool or to the exterior surfaces of the gloved or ungloved hands of the dental practitioner or hygienist and then transmitted to the dental tool or implement, such as an intra-oral camera or an ultraviolet curing light, through contact. More recently, the spread of the hepatitis virus and the acquired immune deficiency virus have caused great concern among dental practitioners, dental hygienists and other staff members not only for their patients, but also for their own health and well-being.

The hepatitis virus and the acquired immune deficiency virus have been found to be carried in or on body fluids and/or tissues. In the environment in which dental practitioners, hygienists and other dental staff members work, i.e. inside the mouth, bodily fluids such as saliva, blood, tissues comprising the gum and portions of the teeth, the pulp and root, etc. may potentially transmit the virus form through contact. The process of cleaning and/or repairing teeth by filling caries, performing a root canal procedure or performing restorative or cosmetic dentistry requires the drilling of the teeth and the subsequent scattering of tissue particles and body fluids about the mouth.

During restorative and cosmetic dental procedures, an intra-oral camera may be inserted into the mouth in order to view particular areas within the mouth which are difficult to view, or which can be seen more clearly through the enlargement provided by the monitor attached to the camera. It is also possible that during restorative and cosmetic dental procedures an ultraviolet curing light may be inserted into the mouth of the patient in order to effect the polymerization of the materials utilized in the restorations of the teeth. Some of the particles and/or fluids which potentially carry disease causing organisms may become attached or adhered to the gloved or ungloved hand of the dental practitioner, hygienist or other dental staff member, or to the unsheathed exterior of the intra-oral camera or the curing light. While it is possible to remove and discard the protective gloves, cleaning and sterilizing the exterior of sensitive electronic or narrow band illumination devices such as the intra-oral camera and ultraviolet curing light, between use on different patients has become a serious problem because of their specialized construction.

During dental procedures ranging from cutting and shaping teeth for receiving caps and/or more extensive bridge work and restoration, or the newer cosmetic dentistry using certain polymers to build up or repair the teeth, the ultraviolet curing light may be placed into the interior of a patient's mouth in close proximity to the tooth or teeth being repaired to effect the curing (or polymerization) of the polymer materials used to restore the tooth or teeth through the use of certain visible lightwaves, i.e. infrared range illumination. The light guide portion of the curing light is placed into the patient's mouth by the dental practitioner or other staff member in order to effect the desired during of the restoration and repair material.

The problem of disease transmission occurs as the curing light is replaced in its holder for subsequent use, possibly on a different patient, without attention to cleaning and sterilization. Anything the light guide may have come into contact with while in the patient's mouth may have become attached to the light guide and be transmitted to the next patient on whom the curing light is used. The mere swabbing down of the light guide with a disinfecting solution will not sterilize the curing light, nor will it kill all of the bacteria and virus forms which may have become attached thereto.

The same is true for an intra-oral camera, containing a dental illumination lamp, which is used by the dental practitioner to illuminate and view, on the associated enlarged video monitor, particular areas of the patient's mouth. Because of the long, narrow tubular construction of the intra-oral camera, and its use either during, intermediate, or subsequent to certain procedures within the patient's mouth, whatever may have been dislodged in the form of tissue or other tooth material or in the form of bodily fluids may become adhered to the exterior of the intra-oral camera and be transmitted to the next patient on whom the camera may be used. As in the earlier case, the swabbing down of the exterior of the camera body with a disinfecting solution will not sterilize it nor will such swabbing kill all of the bacteria and virus forms which may have become attached thereto. The same will be true for a dental illuminating lamp having similar construction (but without the video capabilities) used for illuminating the work place within the patient's mouth.

There have been some attempts to provide sterile sheaths for other dental tools, i.e. the dental handpiece or drill. U.S. Pat. No. 4,266,935 [Hoppe] and U.S. Pat. No. 4,728,290 [Eisner, et al.] provide apparatus which are particularly adapted for use with the dental hand pieces in use today. Neither of these devices address the problem of sheathing either the dental curing light or the intra-oral camera with a sterile shield or barrier which prevents pathogenic contamination but permits the visible lightwaves to be emitted without interruption or wavelength shifting.

There have also been attempts to provide sheaths to other dental or surgical implements, which sheaths provide protection against carrying bacteria and/or virus forms onto the exterior surfaces of the particular implements or tools. U.S. Pat. No. 3,794,091 [Ersek, et al.] discloses a sterile sheath for enclosing an elongated surgical illuminating lamp (endoscope) with a light transmitting lens means disposed at the tip of the light transmitting shaft of the lamp structure. The sheath of Ersek is required to be made of a thermoplastic, thermosetting film in order to provide the necessary durability, rigidity and transparency required of the device. Because the sheath may be inserted through fairly long body canals, the sheath is required to exhibit the described characteristics in order to go around or through obstructions, be sufficiently flexible to bend around turns, curves or corners, yet still retain sterile integrity so that the sheath or barrier is not breached.

Another attempt is that made by U.S. Pat. No. 4,757,381 [Cooper, et al.] which describes a sheath for placement over and around a dental camera. However, the Cooper device does not snugly overlie the dental camera and requires attachment by rotationally twisting the sheath and securing it at either end of the dental camera so that the twisted and rotated sheath remains in that position to achieve the prevention of cross-contamination from patient to patient from subsequent uses of the dental camera. The disclosure particularly describes a transparent, clear plastic material which is used to cover the dental camera, but which material does not exhibit any significant elasticity or strength beyond that necessary to resist minimal tearing when the rotating and twisting motion is utilized to secure the sheath in position.

An attempt to provide a transparent cover to alight ray radiation device was made in U.S. Pat. No. 4,804,240 [Mori]. The description indicates that the cover member which covers the light radiator having a hat-shaped elastic body which is capable of transmitting the visible light ray components transmitted into the optical conductor cable. The cover member, although made to be disposable, may be cleaned and disinfected for repeated use. Since the disclosure describes the cover member being made from a transparent and resilient material, and that the cover member as swordguard-shaped portion (as shown in FIG. 2a) which guard retains its shape, the cover member must be non-elastic.

With all of these earlier patents, there lacks an enabling disclosure which describes for an elastic sheath or barrier, which can be superextended over the exterior surface of a dental tool or implement used in dental or medical procedures, that can simultaneously provide the transmissivity for pre-determined light wavelengths while maintaining the cross-contamination barrier for the named pathogens.

The dental curing light and/or the intra-oral camera and illuminating lamp (as well as other medical devices) are not usually thought of as disease transmission devices. They are customarily cleaned with a disinfecting agent, but not sterilized in the normal course. Some of the light guide elements of curing lights or dental cameras and illuminating lamps are detachable for sterilization in an autoclave. However, detachment and reattachment for purposes of sterilization is not believed to occur with the frequency required (between each patient) as is done for other dental tool and instruments which may be sterilized in an autoclave. Hence, sterilizing most likely does not occur between patients and current practice would lead one to believe that only a disinfectant swabbing of the curing light or camera or illuminating lamp may be done between contact with patients to prevent cross-contamination.

In recent years, dental practitioners, hygienists and other in both the dental and medical professions have become increasingly aware of the rapid spread of communicable diseases borne on body fluids and tissues such as may be dislodged and become attached to dental implements or the gloved or ungloved hands of dental or medical practitioners, hygienists, nurses or other staff members during procedures being performed within the body of a patient. In fact, dental and medical practitioners, along with their respective staff members, have been cautioned to protect themselves from infection by using sterile gloves and masks, and to use protective glasses, when practicing dentistry or other dental procedures on their patients. Recently, the rapid spread of the hepatitis virus and the acquired immune deficiency virus has caused significant concern among these practitioners. The American Dental Association and American medical Association, as well as other professional organizations, have strongly urged that health care practitioners and their staff members take additional steps to decrease the chance of spreading disease by cross-contamination through the use of non-sterile implements.

It is, therefore, an object of the present invention to provide a protective pathogen barrier for tools or implements which may be inserted into the mouth or body of a patient which emit light in a pre-determined wavelength to significantly reduce or prevent the spread or cross-contamination of contagious, communicable diseases.

It is a further object of the present invention to provide such a barrier which is disposable after a single use and which is easily applied and removed so that it would have wide-spread acceptance in the dental and medical professions.

It is a another object of the present invention to provide such a barrier which is highly elastic and stretchable, yet tear-resistant, and which is capable of covering the entirety of a variety of elongated, tubular-shaped dental tools or implements which emit lightwaves in predetermined ranges without interrupting or affecting the emission of such light, or the receiving of reflected light, by use of a lens means to provide the required transmissivity of light during dental or medical procedures.

Other objects will appear hereinafter.

SUMMARY OF THE INVENTION

The present invention may be described as a disposable pathogen barrier for placement over and in proximate contact with a light emitting means for significantly reducing the spread of communicable and infectious diseases which may be transmitted by or through contact with human body fluids and tissues during a first and subsequent use of said light emitting means in conjunction with the treatment of two or more patients eliminating the need for repeated sterilization of said light emitting means between such uses for two or more patients. The disposable pathogen barrier is comprised of an elongated tubular sleeve terminating in a substantially circular aperture at a first end thereof of sufficient size for fitting over said light emitting means and preventing contamination of the outer surfaces of said light emitting means. The barrier also has sufficient elastic material memory to maintain itself in position covering said light emitting means without slippage until manual removal.

The barrier, in a first embodiment, has an optically transmissive second end which overlies in juxtaposition and covers the illumination means of said light emitting means. The optically transmissive second end of said barrier freely passes light rays from said light emitting means without distortion, interruption or light wavelength shifting.

Although the optically transmissive second end of said barrier in the first embodiment may be made from the same material as the sleeve, the optically transmissive second end, in a second embodiment, may be further comprised of an optically clear film inserted into a substantially circular die cut in said sleeve proximal said second end and positioned along the interior surface of said barrier by an adhesive bond around the periphery of said die cut. The adhesive positions the clear film and provides a seal for preventing contamination of the surface of the light emitting means. The optically clear film having a thickness in the range between 0.025 and 0.080 inches.

The barrier may be made from an elastomeric or elastic material, natural or man-made, or combinations thereof. The barrier also exhibits sufficient deformability, toughness and tear-resistance to stretch over said light emitting means and to withstand pulling and stretching during application and removal. The light emitting means may be any one of the group consisting of intra-oral cameras and dental material curing lamps.

BRIEF DESCRIPTION OF THE DRAWINGS

For the purpose of illustrating the invention, there is shown in the drawings forms which are presently preferred;

it being understood, however, that the invention is not limited to the precise arrangements and instrumentalities shown.

FIG. 1 is a side elevational exploded view of the pathogenic barrier of the present invention partially extended and prepared for application over an intra-oral dental camera.

FIG. 2 is a side elevational view of the pathogenic barrier of the present invention as applied over the exterior of an intra-oral dental camera.

DETAILED DESCRIPTION OF THE PREFERRED EMBODIMENTS

Figure 3:
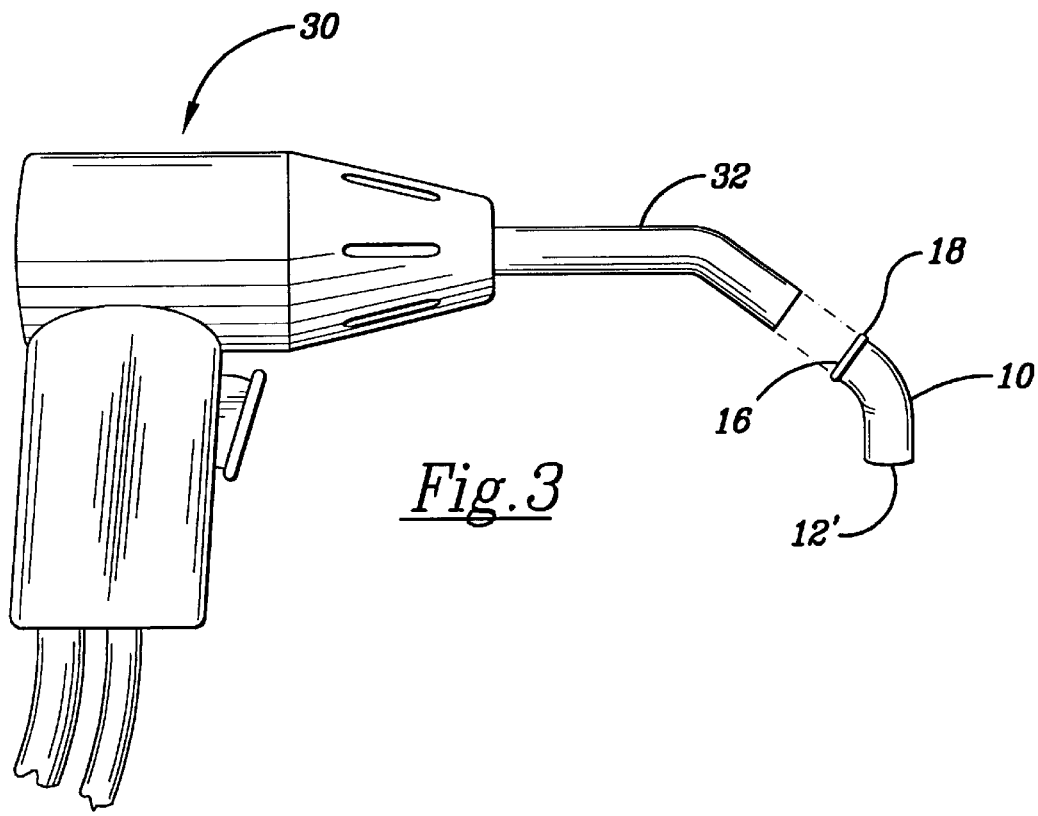
FIG. 3 is a side elevational exploded view of the pathogenic barrier of the present invention partially extended and prepared for application over an infrared curing lamp and lightwave guide.

The following detailed description is of the best presently contemplated mode of carrying out the invention. The description is not intended in a limiting sense, and is made solely for the purpose of illustrating the general principles of the invention. The various features and advantages of the present invention may be more readily understood with reference to the following detailed description taken in conjunction with the accompanying drawings.

Referring now to the drawings in detail, where like numerals refer to like parts or elements, there is shown in FIG. 1, a pathogen barrier or shield 10 having a closed end 12 and has an elongated, tubular body 14. The barrier or shield 10 may be formed from any elastomeric or elastic material, natural or man-made, or any combination thereof. The elastomeric or elastic material should exhibit sufficient deformability to stretch over a variety of differently shaped and sized dental or medical illumination devices as will be described with more particularity below.

The elongated, tubular body or sleeve 14 is formed as a tube with both ends open. The end into which any of the dental or medical devices will be inserted, the proximal end 16, has a beaded lip 18. The other end of the tube will have a round, die-cut hole or aperture into which an optically clear plastic film 20 is positioned. The optically clear plastic film or window 20 (which may be either elastic or non-elastic) has one side coated with an optically clear or translucent adhesive and is adhered within the die-cut end 12 to the sleeve 14. The window 20 is preferred to have a thickness of approximately 0.003 inches, but a thickness in the range of 0.025 inches to 0.080 inches has been found to be acceptable.

The barrier or shield 10 can be provided with the window 20 in position over the die-cut end 12 if usage is to be for sterile individually packaged barriers for medical or dental use. If the barrier or shield 10 is required to provide only an anti-contamination surface, the window 20 can be provided as a separate component on a continuous dispenser roll to be positioned and adhered in place by the user. Since the barrier or shield 10 is to be placed in position over the medical or dental implement by unrolling the elasticized barrier over the exterior surface of the implement, the user is able to firmly adhere the window 20 onto the internal surface of the sleeve 14 around the die-cut end 12 to form an adhesive bond between the sleeve 14 and the window 20 at the die cut end 12, which bond provides a seal sufficient to prevent the contamination of the medical or dental implement to be shielded during use. Then the barrier or shield 10 can be applied to the medical or dental implement as described.

With reference to FIGS. 1 and 2, an intra-oral dental camera 22 is shown having light guide sheath 24 entering the body at a first end of the camera 22. At the opposite end of the camera 22 there are mounted a pair of illuminating lamps 26a, b bracketing the fiber optic receptor 28 for capturing the reflected light images and transmitting that light for display on a video monitor. Both the "white" light for purposes of illumination through lamps 26a, b and the reflected image captured by the receptor 28 are transmitted through the light guide sheath 24 to equipment for controlling the illumination and for displaying the image. This equipment is not deemed to be part of this invention, and neither are the hand controls mounted to the dental camera 22, and, therefore, they are omitted from this description.

The sheath or barrier 10 is applied to the dental camera 22 by stretching it over the end of the camera which carries the lamps 26a, b and the receptor 28 and then unrolling and stretching the sheath 10 over the remainder of the exterior surface of the camera 22. The sheath or barrier 10 is shown fully mounted to the dental camera 22 in FIG. 2. The window 20, when the barrier or shield 10 is unrolled and stretched into position on the dental camera 22, extends over and covers the portion of the dental camera 22 which carries the illuminating lamps 26a, b and the reflected light image receptor 28.

With specific reference to FIG. 2, the dental camera 22, including the illuminating lamps 26a, b and the reflected light image receptor 28, require the free passage of the visible light rays necessary to illuminate the desired area of the mouth and to receive the reflected light from the designated area without distortion, interruption or light wavelength shifting. This is accomplished by positioning the window 20 in approximate juxtaposition covering the illuminating lamps 26a, b and the reflected light image receptor 28 of the dental camera 22 such that the window 20 does not impair any transmissivity of the illuminating light or the detection of reflected light from the designated surface areas in the mouth of the patient. Hence, the window 20 must exhibit the characteristic of optical transparency for the purposes of illuminating and receiving the reflected light from the designated area. In order to assist in maintaining optical transparency of the window 20, the material utilized to form the window must exhibit sufficient flexibility such that it will conform to the shape of the end of the dental camera 22 when extending over that end during application and during use.

Figure 4:
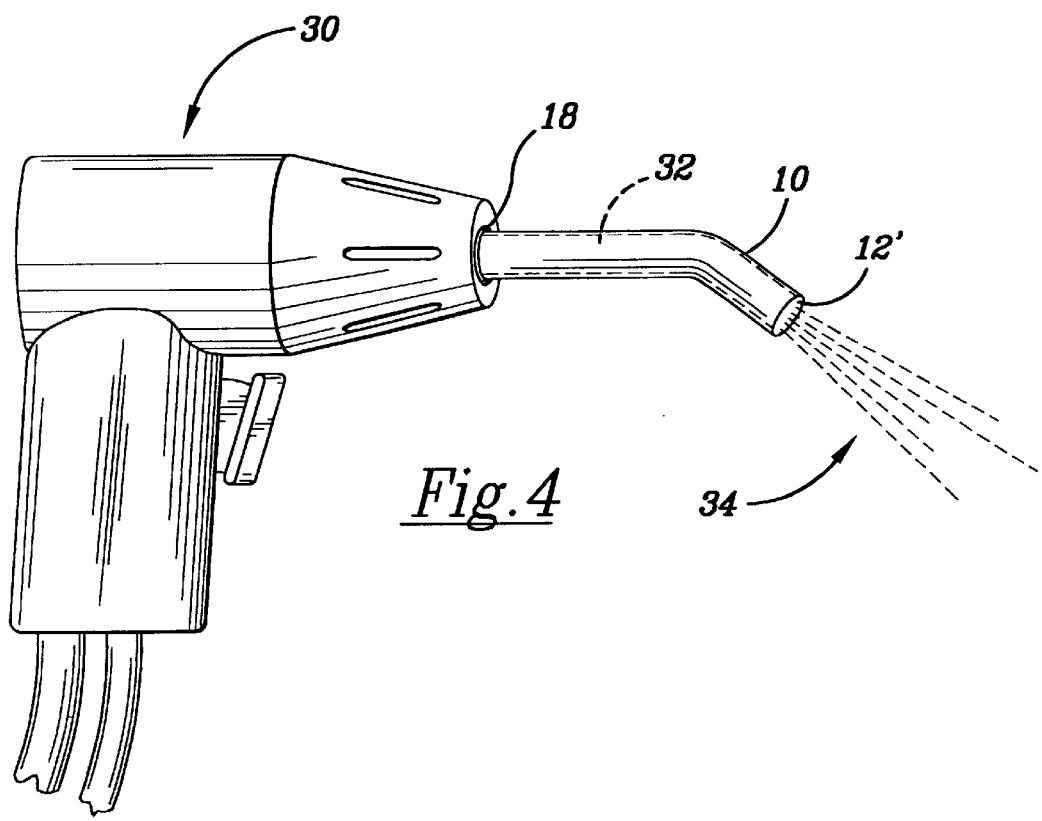
FIG. 4 is a side elevational view of the pathogenic barrier of the present invention as applied over the exterior of an infrared curing lamp and lightwave guide.

In showing a different configuration of a light guide means over which the barrier or sheath 10 may be applied, reference may be had to FIGS. 3 and 4 for use in describing the application of the barrier 10 to a dental curing light. The barrier or shield 10 is shown in a partially unrolled position separated from the curved light guide means 32 of the dental curing light 30. Mounting and positioning of the barrier or shield 10 is accomplished in a similar manner as was done with the dental camera. The barrier or shield 10 is stretched over the illuminating end of the light guide means 32 and then unrolled and stretched back along and over the light guide means 32. Since only the light guide means 32 is intended to be inserted into the mouth of a patient, the body, switch means and light fiber sheathing are not covered. Since only one model of a dental ultraviolet curing lamp is being shown in FIGS. 3 and 4, it should not be assumed that the use of the barrier or sheath 10 is limited to this particular form. The barrier or sheath of the present invention is usable on other dental curing lamps for covering the light guide means extending into the patient's mouth as all of these light guide means have similar elongated tubular shapes which are either straight or slightly bent as the light guide means 32 shown in FIGS. 3 and 4.

With specific reference to FIG. 4, the infrared or ultraviolet light rays 34 are shown emanating from the end of the light guide means 32. These light rays 34 are transmitted through the barrier or shield 10 without interruption, and with little or no distortion or wavelength shifting, of the emitted light. This is accomplished by one of two means. The barrier or shield 10 may include the window 20 in the die-cut end 12 of the barrier 10. A second form of the barrier or shield 10 of the present invention eliminates the necessity for including the window 20 and merely provides a closed end 12' for the barrier or shield 10. This closed end 12' permits the transmission of the infrared or ultraviolet light wavelengths through the optically clear barrier or shield 10 without distortion, interruption or wavelength shifting, and without the need for creating a die-cut in the end of the barrier or sheath 10 to accommodate the window 20. The die-cut increases the possibility of a barrier breach through loss of adhesion at the junction between the die-cut end 12 hole and the periphery of the window 20 and also increases the distortion, interruption and wavelength shifting of the light rays 34 along the seat or joint. Thus, the window 20 restricts the use of the barrier or sheath 10 by creating a significant problem with diffusion of the light rays 34 through and about the seal line.

The barrier or sheath 10 must, then, be of a continuous form such that the material of the barrier or sheath 10 extends over and covers the end 12' so as to eliminate any possible light diffusion or defraction through the joint or seal of the window 20 to the barrier or sheath 10. It is presently known that a barrier or shield 10 made from co-extruded polyethylene film having a window which is heat sealed at the distal end in order to provide an optically transparent portion of the barrier or sheath 10 to the illuminating end of the light guide means 32 creates significant light diffraction and/or diffusion on and about the heat seal line between the window 20 and the polyethylene film. It is necessary in the dental field for a practitioner to fully cure new composite materials which are adhered to and into teeth of a patient. The exposure of the new composite materials to the light rays 34 and, more particularly, the efficacy or depth of cure, is directly related to the transmissivity of the light rays 34 through the barrier or sheath 10 without obstruction, distortion, interruption or wavelength shifting. It is recommended, and believed necessary, that the proper cure light wavelength falls within the range of at lease 500–800 nanometers. The described co-extruded polyethylene film shield having a window with heat seal line is not capable of reaching the recommended and consistent wavelength due to significant light loss through the material.

The present invention is preferred to be constructed from dipped polyurethane, which creates a continuous barrier or sheath 10, having a thickness in the range of 2–3 microns, which creates an optically transparent or clear barrier without the need for a window 20. An evaluation of both constructions of the described barriers or sheaths 10, in order to determine ultraviolet light loss when installed over the light guide means 32 of a dental curing light 30 produced the following results. The test procedure followed was to allow the power supply of the dental curing light 30 to stabilize after a warm-up period of approximately 15 minutes in order to assure uniform output from the light guide means 32. The output of the dental curing light 30, through the light guide means 32, was measured both before and after each sample was applied over the light guide means 32 in order to minimize any fluctuations in the wavelengths emanating from the dental curing light 30. The same number of samples of each type were tested with the identical light meter to determine light loss through the respective materials in $mw/cm_2$ with the test results being as shown in the Table below.

| Shield Type | UV Light Loss $(mx/cm_2)$ | Testing Repetitions |
| --- | --- | --- |
| Co-extruded polyethylene film with heat seal window | 59 | 15 |
| Dipped polyurethane (continuous) | 38 | 15 |

The results shown above in the Table are average light loss results which reveal that the co-extruded polyethylene film has light losses 155% greater than the dipped polyurethane continuous barrier of the present invention. Based upon the test results, the co-extruded polyethylene film barrier is not capable, without significant extension of time for curing the new composite polymeric materials used by dental practitioners to effectively reach the depth of cure of those materials which extend below the surface far into the teeth of a patient. This is believed due to detraction and diffusion of the ultraviolet light rays 34 at or about the heat seal line, as well as the inability of the particular material, the polyethylene film, to be optically transparent to the light rays 34. Thus, the efficacy of the cure using the co-extruded polyethylene film is not at the recommended level, and does not fall within the range of the light wavelength to be transmitted, 500–800 nanometers, such that extended exposure times will be necessary in order to meet the requirements of the manufacturers of the new composite polymeric materials used in filling and bonding teeth. On the other hand, the dipped polyurethane material of the present invention meets the requirements by permitting the transmissivity of the light rays 34 through the material such that the UV light rays 34 remain within the recommended wavelength of 500–800 nanometers which will not require the extension of the time necessary to provide the depth of cure recommended by the manufacturer of the new composite polymeric materials.

In this manner, the pathogen barrier or shield 10 of the present invention presents an optically transparent end 12 which may either contain the window 20 or the material of the barrier or sheath 10 may be substantially optically transparent and present a closed end 12', both capable of extending over and covering the end of the medical or dental tool or implement being inserted into an opening or canal of a patient. Further, with regard to the embodiment of the invention which contains the optically transparent window 20, each barrier or sheath 10 can be completely assembled by the manufacturer to provide a sterile sheath, or the window 20 of the optically transparent material can be placed within and adhered to the end 12 of the sleeve 14 and assembled on sight by a dental or medical practitioner, or such practitioner's staff, which enables the manufacturer to construct the tube or sleeve 14 out of the material which is not necessarily optically transparent. Hence, the sheath or barrier 10 providing an optically transparent end for specialized medical or dental tools or implements has been described in its various embodiments, and with explanations as to particular usage to maintain the appropriate functioning and capabilities of the light sensitive apparatus which it covers.

The present invention may be embodied in other specific forms without departing from the spirit or essential attributes thereof and, accordingly, the described embodiments are to be considered in all respects as being illustrative and not restrictive, with the scope of the invention being indicated by the appended claims, rather than the foregoing detailed description, as indicating the scope of the invention as well as all modifications which may fall within a range of equivalency which are also intended to be embraced therein.

I claim:

1. A disposable pathogen barrier for placement over and in proximate contact with a light emitting end of a light guide means of a dental material curing lamp for significantly reducing the spread of communicable and infectious diseases which may be transmitted by or through contact with human body fluids and tissues during a first and subsequent use of said dental material curing lamp in conjunction with the treatment of two or more patients eliminating the need for repeated sterilization of said dental material curing lamp between such uses for two or more patients comprising an elongated tubular sleeve made in continuous dipped form from polyurethane terminating in a substantially circular aperture at a first end thereof and having an optically transmissive second end capable of freely passing emitted light rays from said light emitting means in the range of 500–800 manometers for illuminating a designated area to expose composite dental material to said light rays and cure said composite dental material without distortion, interruption or wavelength shifting, and for fitting over said light emitting means and preventing contamination of the outer surfaces of said light emitting means and said dental material curing lamp, said barrier having sufficient elastic material memory to maintain itself in position covering said light guide means without slippage until manual removal.

2. In accordance with claim 1, wherein said optically transmissive second end of said disposable pathogen barrier for overlying in juxtaposition and covering the light emitting end of the light guide means of said dental curing lamp.

3. In accordance with claim 1, wherein said disposable pathogen barrier having a thickness in the range between 2–3 microns.

4. In accordance with claim 1, wherein said disposable pathogen barrier exhibits sufficient deformability, toughness and tear-resistance to stretch over said light emitting means and to withstand pulling and stretching during application and removal.

* * * * *